US006548049B1

(12) United States Patent
Cutie et al.

(10) Patent No.: US 6,548,049 B1
(45) Date of Patent: *Apr. 15, 2003

(54) MEDICINAL AEROSOL FORMULATION

(75) Inventors: Anthony J. Cutie, Bridgewater, NJ (US); Akwete L. Adjei, Bridgewater, NJ (US); Frederick A. Sexton, Fair Haven, NJ (US)

(73) Assignee: Aeropharm Technology Incorporated, Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/702,201

(22) Filed: Oct. 31, 2000

Related U.S. Application Data

(60) Provisional application No. 60/201,229, filed on May 1, 2000.

(51) Int. Cl.[7] .................. A61M 11/00; A61M 18/00; A61P 7/12; A61K 9/12; A01N 25/06
(52) U.S. Cl. .................. 424/45; 424/44; 424/43; 514/4; 514/866; 128/200.14; 128/200.21; 128/200.23
(58) Field of Search .................. 424/45, 44, 43; 514/4, 866; 128/200.14, 200.21, 200.23

(56) References Cited

U.S. PATENT DOCUMENTS

| | | | |
|---|---|---|---|
| 5,011,678 A | | 4/1991 | Wang et al. |
| 5,594,015 A | * | 1/1997 | Kurtz et al. ............... 514/369 |
| 5,688,782 A | | 11/1997 | Neale et al. |
| 5,744,123 A | * | 4/1998 | Akehurst et al. ............ 424/45 |
| 6,193,954 B1 | | 2/2001 | Adjei et al. |

FOREIGN PATENT DOCUMENTS

| WO | WO 90 009781 A | 9/1990 |
|---|---|---|
| WO | WO 96 19198 A | 6/1996 |

OTHER PUBLICATIONS

Evans, A. J., Krentz, A. J.; Recent Developments and Emerging Therapies for Type 2 Diabetes Mellitus; Aug., 1999; Drugs in R&D; 2(2), 75–94; See: abstract.*

Reasner, C. A. II, Promising New Approaches, Blackwell Science Ltd., Diabetes, Obes. Metab., 1 (Suppl. 1), S41–S48, (1999) See: Abstract.*

Patton et al., Advanced Drug Delivery Reviews, 8(1992) 179–196.

* cited by examiner

*Primary Examiner*—Frederick Krass
*Assistant Examiner*—Clinton Ostrup
(74) *Attorney, Agent, or Firm*—Frommer Lawrence & Haug LLP

(57) ABSTRACT

This invention relates to a medicinal aerosol formulation and more particularly, to a medicinal aerosol formulation containing pioglitazone medicament and a fluid carrier.

36 Claims, No Drawings

MEDICINAL AEROSOL FORMULATION

This application claims priority from U.S. provisional application Serial No. 60/201,229 filed May 1, 2000, which is incorporated herein by reference.

BACKGROUND OF THE INVENTION

1. Field of the Invention

This invention relates to a medicinal aerosol formulation, and more particularly, to a medicinal aerosol formulation comprising a pioglitazone hydrochloride.

2. Description of the Related Art.

Delivery of drugs to the lung by way of inhalation is an important means of treating a variety of conditions, including such common local conditions as cystic fibrosis, pneumonia, bronchial asthma and chronic obstructive pulmonary disease and some systemic conditions, including hormone replacement, pain management, immune deficiency, erythropoiesis, diabetes, etc. Anti-diabetic drugs, e.g. an insulin, are among the drugs that are administered to the lung for such purposes. Such drugs are commonly administered to the lung in the form of an aerosol of particles of respirable size (less than about 10 μm in diameter). The aerosol formulation can be presented as a liquid or a dry powder. In order to assure proper particle size in a liquid aerosol, particles can be prepared in respirable size and then incorporated into a colloidial dispersion either containing a propellant as a metered dose inhaler (MDI) or air, such as in the case of a dry powder inhaler (DPI). Alternatively, formulations can be prepared in solution form in order to avoid the concern for proper particle size in the formulation. Solution formulations must nevertheless be dispensed in a manner that produces particles or droplets of respirable size.

For MDI application, once prepared an aerosol formulation is filled into an aerosol canister equipped with a metered dose valve. In the hands of the patient the formulation is dispensed via an actuator adapted to direct the dose from the valve to the patient.

What is needed and desired is a stable aerosol formulation for the treatment of diabetes and conditions related thereto.

SUMMARY OF THE INVENTION

It has surprisingly been found that a novel and stable medicinal aerosol formulation of an anti-diabetic medicament can be obtained without the use of a surfactant, such as sorbitan trioleate. The medicament is pioglitazone and its salts or esters such as, for example maleate, hydrochloride, etc., or other pharmaceutically acceptable forms. This medicament may be used alone or combined with a suitable β-cell hypoglycemic selected from the group consisting of an amylin and insulin, as well as, other medicament agents possessing antidiabetic activity, including the α-cell hypoglycemic glucagon, acetohexamide, chlorpropamide, tolazamide, tolbutamide, and glipizide, as well as inclusion of any mixture of any two or three of the foregoing β-cell hypoglycemic medicaments.

DETAILED DESCRIPTION OF THE INVENTION

This application makes reference to U.S. application Ser. No. 09/209,228 filed Dec. 10, 1998, now U.S. Pat. No. 6,261,539B1, which is incorporated hereinto by reference in its entirety.

This invention involves a stable aerosol formulation suitable for delivery which comprises (a) a pioglitazone medicament, and (b) a suitable fluid carrier. The pioglitazone, e.g. hydrochloride, may be present as a single drug or in combination with a suitable β-cell hypoglycemic, such as an amylin and an insulin and their derivatives and the α-cell hypoglycemic glucagon.

A suitable β-cell hypoglycemic medicament is one selected from either an amylin or an insulin and any of their derivatives. A suitable synthetic, antidiabetic agent is one selected from an acetohexamide, chlorpropamide, tolazemide, tolbutamide, glipizide, glyburide, glucophage, phentolamine, etc., and a mixture of any two or three of the foregoing medicaments.

The tern "insulin" shall be interpreted to encompass natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution.

The terms "insulin analog," "monomeric insulin" and the like are used interchangeably herein and are intended to encompass any form of "insulin" as defined above wherein one or more of the amino acids within the polypeptide chain has been replaced with an alternative amino acid and/or wherein one or more of the amino acids has been deleted or wherein one or more additional amino acids has been added to the polypeptide chain or amino acid sequences which act as insulin in decreasing blood glucose levels. In general, the "insulin analogs" of the present invention include "insulin lispro analogs," as disclosed in U.S. Pat. No. 5,547,929, incorporated hereinto by reference in its entirety, insulin analogs including LysPro insulin and humalog insulin, and other "super insulin analogs", wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs, which are insulin-like compounds used for the same general purpose as insulin such as insulin lispro i.e., compounds which are administered to reduce blood glucose levels.

An "amylin" includes natural human amylin, bovine, porcine, rat, rabbit amylin, as well as synthetic, semi-synthetic or recombinant amylin or amylin analogs including pramlintide and other amylin agonists as disclosed in U.S. Pat. No. 5,686,411, and U.S. Pat. No. 5,854,215, both of which are incorporated hereinto by reference in their entirety.

For purposes of the formulations of this invention, which are intended for inhalation into the lungs, the pioglitazone medicament, e.g. pioglitazone hydrochloride, and the other medicament (when present) are preferably micronized whereby a therapeutically effective amount or fraction (e.g. ninety percent or more) of the medicament is particulate. Typically, the particles have a diameter of less than about 10 microns, and preferably less than about 5 microns, in order that the particles can be inhaled into the respiratory tract and/or lungs.

The particulate pioglitazone hydrochloride medicament or drug is present in the inventive formulations in a therapeutically effective amount, that is, an amount such that the drug can be administered as a dispersion or an aerosol, such as topically, or via oral or nasal inhalation, and cause its desired therapeutic effect, typically preferred with one dose, or through several doses. The pioglitazone hydrochloride medicament is administered as an aerosol from a conventional valve, e.g., a metered dose valve, through an aerosol adapter also known as an actuator.

The term "amount" as used herein refers to quantity or to concentration as appropriate to the context. The amount of pioglitazone hydrochloride medicament or mixture of medicaments including pioglitazone hydrochloride that constitutes a therapeutically effective amount varies according to factors such as the potency of the particular medicament or medicaments used, the route of administration of the formulation, and the mechanical system used to administer the formulation. A therapeutically effective amount of pioglitazone hydrochloride, alone or combined, can be selected by those of ordinary skill in the art with due consideration of such factors. Generally a therapeutically effective amount of pioglitazone hydrochloride will be from about 0.010 parts by weight to about 20 parts by weight based on 100 parts by weight of the fluid carrier e.g. propellant.

A suitable fluid carrier is selected. A suitable fluid carrier includes air, a hydrocarbon, such as n-butane, propane, isopentane, etc. or a propellant. A suitable propellant is any fluorocarbon, e.g. a 1–6 hydrogen containing flurocarbon such as $CHF_2CHF_2$, $CF_3CH_2F$, $CH_2F_2CH_3$ and $CF_3CHFCF_3$; a perfluorocarbon, e.g. a 1–4 carbon perfluorocarbon, such as $CF_3CF_3$, $CF_3CF_2CF_3$; or any mixture of the foregoing, having a sufficient vapor pressure to render them effective as propellants. Some typical suitable propellants include conventional chlorofluorocarbon (CFC) propellants such as propellants 11, 12 and 114 or a mixture of any of the foregoing propellants. Non-CFC propellants such as 1,1,1,2-tetrafluoroethane (Propellant 134a), 1,1,1,2,3,3,3-heptafluoropropane (Propellant 227) or mixtures thereof are preferred. The propellant is preferably present in an amount sufficient to propel a plurality of the selected doses of the drug from an aerosol canister.

Optionally, a suitable stabilizer is selected. A suitable stabilizer is a "water addition". As used herein a "water addition" is an amount of water which (1) is added, either initially with other components of the aerosol formulation, e.g. the pioglitazone hydrochloride medicament, and fluid carrier, or after the other components, e.g. medicament, fluid carrier, are combined and processed, (2) is in addition to the water which is always present and which develops during processing and/or storage of the aerosol formulation, i.e. "developed" or "nascent" formulation water, and (3) is present in an amount which further stabilizes a medicinal aerosol formulation having nascent formulation, e.g. of pioglitazone hydrochloride water.

An aerosol formulation preferably comprises the water addition in an amount effective to more effectively stabilize the formulation relative to an identical formulation not containing the water addition, i.e. containing only nascent formulation water, such that the drug, e.g. pioglitazone hydrochloride, does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

The particular amount of the water addition that constitutes an effective amount is dependent upon the particular fluid carrier, e.g. propellant, and on the particular drug or drugs used in the formulation. It is therefore not practical to enumerate specific effective amounts for use with specific formulations of the invention, but such amounts can readily be determined by those skilled in the art with due consideration of the factors set forth above. Generally, however, the water addition must be present in a formulation in an amount in excess of the concentration of the nascent formulation water. Such concentration of nascent formulation water typically ranges up to 300 parts by weight per one million parts by weight of the total weight of the aerosol formulation. Accordingly, the water addition in excess of this nascent water concentration typically ranges from about 10 parts by weight to 5000 parts by weight per one million parts by weight of the total aerosol formulation weight. Most preferred is that the concentration of the water addition in excess of this nascent water concentration is from 500 parts by weight to 5000 parts by weight per one million parts by weight of the total weight of the medicinal aerosol formulation.

It is to be emphasized that this is an amount which exceeds the amount of nascent or developed formulation water. It is also to be stressed that preferably this amount of water addition can be added and initially combined with the other components of the formulation, e.g. pioglitazone hydrochloride and fluid carrier, e.g. 1,1,1,2-tetrahydrofluoroehtane. However, the water addition can be added to the resultant formulation after these other components have been processed, e.g. prior to or subsequent to storage.

It has surprisingly been found that the pioglitazone hydrochloride formulation of the invention is stable without the necessity of employing a cosolvent, such as ethanol, or surfactants. However, further components, such as conventional lubricants or surfactants, cosolvents, ethanol, etc., can also be present in an aerosol formulation of the invention in suitable amounts readily determined by those skilled in the art. In this regard, reference is made to U.S. Pat. No. 5,225,183, which is incorporated by reference hereinto in its entirety. Typically, a co-solvent such as ethanol is added in an amount ranging from 0.5 to 10% by weight of the total weight of the formulation.

A most preferred formulation comprises the pioglitazone hydrochloride medicament, the fluid carrier, e.g. 1,1,1,2-tetrafluoroethane, the cosolvent, e.g ethanol and the water addition.

Generally the formulations of the invention can be prepared by combining (i) the pioglitazone hydrochloride drug or pioglitazone hydrochloride drugs in an amount sufficient to provide a plurality of therapeutically effective doses; (ii) the fluid, e.g. propellant, in an amount sufficient to propel a plurality of doses, e.g. from an aerosol canister; (iii) optionally, the water addition in an amount effective to further stabilize each of the formulations; and (iv) any further optional components e.g. ethanol as a cosolvent; and dispersing the components. The components can be dispersed using a conventional mixer or homogenizer, by shaking, or by ultrasonic energy as well as by the use of a bead mill or a microfluidizer. Bulk formulations can be transferred to smaller individual aerosol vials by using valve to valve transfer methods, pressure filling or by using conventional cold-fill methods. It is not required that a component used in a suspension aerosol formulation be soluble in the fluid carrier, e.g. propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular component and other adjuvants used (if any), on the fluid, e.g. propellant, and on the particular drug being used. Conventional neoprene and buna valve rubbers used in metered dose valves for delivering conventional CFC formulations often have less than optimal valve delivery characteristics and ease of operation when used with formulations containing HFC-134*a* or HFC-227.

Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as Vistalonl™ (Exxon), Royalene™ (UniRoyal), bunaEP (Bayer). Also suitable are diaphragms fashioned by extrusion, injection molding or compression molding from a thermoplastic elastomeric material such as FLEXOMER GERS 1085 NT polyolefin (Union Carbide).

Conventional aerosol canisters, coated or uncoated, anodized or unanodized, e.g., those of aluminum, glass, stainless steel, polybutyl or polyethylene terephthalate, and coated canisters or cans with epon, epoxy, etc., can be used to contain a formulation of the invention.

The formulation of the invention can be delivered to the respiratory tract and/or lung by oral inhalation in order to treat diabetes and a diabetes related condition susceptible of treatment by inhalation. The formulations of the invention can also be delivered by nasal inhalation in order to treat, e.g., diabetes (systemic), or they can be delivered via oral (e.g., buccal) administration in order to treat, e.g., diabetes and a diabetes related condition.

We claim:

1. A nonaqueous aerosol formulation, which comprises:

(a) a therapeutically effective amount of pioglitazone medicament;

(b) a nonaqueous fluid propellant carrier; and (c) added thereto, a water addition stabilizer present in an amount which is in addition to nascent formulation water.

2. The formulation as defined in claim 1 wherein said pioglitazone medicament is pioglitazone hydrochloride which is combined with a second medicament comprising an amylin.

3. The formulation as defined in claim 2 wherein said second medicament further comprises a synthetic antidiabetic agent.

4. The formulation as defined in claim 3 wherein said agent is selected from the group consisting of glucagon, acetohexamide, chlorpropamide, tolazemide, tolbutamide, glipizide, glyburide, glucophage, phentolamine, and a mixture of any of the foregoing agents.

5. The formulation as defined in claim 4 wherein the second medicament is combined with glucagon.

6. A method of preparing a nonaqueous medicinal aerosol formulation according to claim 1, which comprises:

(a) combining (i) said pioglitazone medicament in an amount sufficient to provide a plurality of therapeutically effective doses and (ii) said nonaqueous fluid propellant carrier in an amount sufficient to propel said plurality of said therapeutically effective doses from an aerosol canister; and (iii) said water addition stabilizer added to (i) and (ii) in an effective stabilizing amount; and (b) dispersing components (i), (ii) and (iii).

7. The method as defined in claim 6 which further comprises combining in step (a) a cosolvent and in step (b) dispersing components (i), (ii) and (iii) with said cosolvent.

8. The method as defined in claim 7 wherein said cosolvent is ethanol.

9. The formulation as defined in claim 1 which further includes a cosolvent.

10. The formulation as defined in claim 9 wherein said cosolvent comprises ethanol.

11. A nonaqueous aerosol formulation, which consists essentially of:

(a) a therapeutically effective amount of a pioglitazone medicament;

(b) a nonaquecus fluid propellant carrier;

(c) a second medicament selected from the group consisting of an amylin, an insulin and a mixture of the foregoing; and (d) added thereto, a water addition stabilizer present in an amount which is in excess of nascent formulation water.

12. The formulation as defined in claim 11 wherein said second medicament comprises an amylin.

13. The formulation as defined in claim 11 wherein said second medicament is an insulin.

14. The formulation as defined in claim 1 or claim 11 wherein said fluid propellant carrier is selected from the group of propellants consisting of 1,1,1,2-tetrafluoroethane, 1,1,1,2,3,3,3-heptafluoropropane or a mixture thereof.

15. The formulation as defined in claim 1 or claim 11 wherein said fluid propellant carrier is a compressed gas selected from the group consisting of air, carbon dioxide, nitrogen, and a mixture of any of the foregoing compressed gases.

16. The formulation as defined in claim 1 or claim 11 wherein said fluid propellant carrier is a hydrocarbon selected from the group consisting of n-butane, propane, isopentane and a mixture of any of the foregoing hydrocarbons.

17. An aerosol canister equipped with a metered dose valve, containing a nonaqueous formulation according to claim 1 or claim 11.

18. A method of treating or controlling diabetes or a diabetes related condition, in a human or an animal capable of being treated by oral or nasal inhalation, said method comprising, administering a formulation accordingly to claim 1 or claim 11 to said human or animal by oral or nasal inhalation.

19. A nonaqueous aerosol formulation, which consists essentially of:

(a) a therapeutically effective amount of a pioglitazone medicament;

(b) a nonaqueous fluid propellant carrier;

(c) a second medicament selected from the group consisting of an amylin, an insulin and a mixture of the foregoing; and (d) added thereto, a stabilizer comprising a water addition which is in an amount which (1) is in excess of nascent formulation water and (2) is present in an amount sufficient to stabilize the formulation to prevent settling, creaming or flocculation for a time sufficient to allow reproducible dosing of said pioglitazone medicament after agitation of the formulation.

20. A method of stabilizing a nonaqueous aerosol formulation, comprising (a) a therapeutically effective amount of pioglitazone medicament; and (b) a nonaqueous fluid propellant carrier, which comprises:

adding thereto, a water addition stabilizer present in an amount which is in addition to nascent formulation water.

21. The method as defined in claim 20 wherein said formulation further comprises a second medicament comprising an amylin.

22. The method as defined in claim 20 wherein said formulation further comprises an antidiabetic agent selected from the group consisting of glucagon, acetohexamide, chlorpropamide, tolazemide, tolbutamide, glipizide, gluburide, glucophage, phentolamine and a mixture of any of the foregoing agents.

23. A metered dose inhaler containing a nonaqueous medicinal aerosol formulation, the formulation comprising:
   (a) a pioglitazone drug in particulate form in a therapeutically effective amount;
   (b) a nonaqueous fluid propellant carrier; and
   (c) added thereto, a stabilizer comprising a water addition which is present in an amount which (1) is in excess of nascent formulation water and (2) is present in an amount sufficient to stabilize the formulation to prevent settling, creaming or flocculation for a time sufficient to allow reproducible dosing of said pioglitazone drug after agitation of the formulation.

24. The metered dose inhaler as defined in claim 23 wherein said pioglitazone drug is combined with a second drug which is an amylin.

25. The metered dose inhaler as defined in claim 24 where said second drug further comprises a synthetic antidiabetic medicament.

26. The metered dose inhaler as defined in claim 25 wherein said synthetic antidiabetic medicament is selected from the group consisting of glucagon, acetohexamide, tolbutamide, glipizide, glyburide, glucophage, phentolamine, and a mixture of any of the foregoing medicaments.

27. The metered dose inhaler as defined in claim 23 which further comprises a second drug which is glucagon.

28. The metered dose inhaler as defined in claim 27 wherein said second drug further comprises a mixture of an amylin and insulin.

29. The metered dose inhaler as defined in claim 23 wherein said formulation further includes a cosolvent.

30. The metered dose inhaler as defined in claim 29 wherein said cosolvent is ethanol.

31. The metered dose inhaler as defined in claim 23 wherein said pioglitazone drug is pioglitazone hydrochloride and said stabilizer is present in said excess in an amount of about 10 parts by weight to about 5000 parts by weight based on one million parts by total weight of the medicinal aerosol formulation.

32. The metered dose inhaler as defined in claim 23 wherein said fluid propellant carrier is a propellant selected from the group consisting of 1,1,1,2-tetrafluoroethane, 1,1,1,2,3,3,3-heptafluoropropane or a mixture thereof.

33. The metered dose inhaler as defined in claim 23 wherein said fluid propellant carrier is a hydrocarbon selected from the group consisting of n-butane, propane, isopentane and a mixture of any of the foregoing hydrocarbons.

34. A metered dose inhaler containing a nonaqueous medicinal aerosol formulation which consists essentially of:
   (a) a pioglitazone drug in particulate form in a therapeutically effective amount combined with a second drug which is selected from the group consisting of an amylin, an insulin and a mixture of the foregoing;
   (b) a nonaqueous fluid propellant carrier; and
   (c) added thereto, a stabilizer comprising a water addition present in an amount which is in excess of nascent formulation water.

35. The metered dose inhaler as defined in claim 34 wherein said second drug comprises an amylin.

36. The metered dose inhaler as defined in claim 34 wherein said second drug comprises insulin.

* * * * *